United States Patent [19]

Shaber et al.

[11] Patent Number: 5,397,793
[45] Date of Patent: Mar. 14, 1995

[54] HETEROCYCLICACETONITRILES AND FUNGICIDAL USE

[75] Inventors: Steven H. Shaber, Horsham; Edward M. Szapacs, Center Valley; Charles H. Reynolds, Lansdale, all of Pa.

[73] Assignee: Rohm and Haas Company, Philadelphia, Pa.

[21] Appl. No.: 152,555

[22] Filed: Nov. 15, 1993

Related U.S. Application Data

[63] Continuation of Ser. No. 491,782, Mar. 12, 1990, abandoned.

[51] Int. Cl.$^6$ .................... C07D 405/06; A61K 31/44
[52] U.S. Cl. ............................ 514/336; 514/357; 514/242; 514/256; 514/255; 514/247; 546/330; 546/283; 546/284; 544/215; 544/180; 544/238; 544/333; 544/335; 544/405
[58] Field of Search .................. 546/330, 283, 284; 514/336, 357

[56] References Cited

U.S. PATENT DOCUMENTS 3,397,273  8/1968  Van Heyningen et al. ........ 546/330
4,398,942  8/1983  Ikari et al. ............................ 504/239

Primary Examiner—Jane T. Fan
Attorney, Agent, or Firm—Joseph F. Leightner

[57] ABSTRACT

A class of novel heterocyclicacetonitriles which is useful in the control of fungi, especially bitunicate asci and unitunicate asd, has been discovered. These compounds are of the general formula:

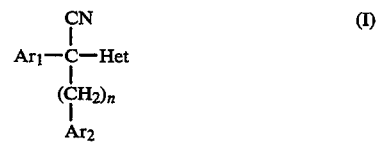

wherein $Ar_1$ and $Ar_2$ are substituted or unsubstituted aryl groups; Het is a six-membered nitrogen-containing heterocyclic ring; n is the integer 2 or 3; and the agronomically acceptable enantiomorphs, add addition salts and metal complexes thereof.

12 Claims, No Drawings

HETEROCYCLICACETONITRILES AND FUNGICIDAL USE

This is a continuation of application Ser. No. 491,782, filed Mar. 12, 1990, now abandoned.

BACKGROUND OF THE INVENTION

1. Field of the Invention

This invention relates to novel heterocyclicacetonitrile derivatives, and enantiomorphs, salts and metal salt complexes thereof and their use as broad spectrum fungicides.

2. Description of the Prior Art

Taylor, et al., U.S. Pat. No. 3,818,009; U.S. Pat. No. 3,868,244, and U.S. Pat. No. 3,887,708, describe a series of alpha-disubstituted-5-pyrimidine methanes which are useful as plant growth regulators and fungicides. They prepared one cyanide compound: $\alpha$-, $\alpha$-diphenyl-(5-pyrimidyl)acetonitrile. Taylor and Holden, U.S. Pat. No. 3,544,682, disclose a fungicidal method employing substituted pyrazines. In the course of this work $\alpha$-, $\alpha$-diphenyl-pyrazinyl-acetonitrile was claimed as a fungicide.

Van Heyninagen and Taylor, U.S. Pat. No. 3,397,273 disclose a broad class of 3-pyridyl methane derivatives as fungicides. Nitrile compounds are disclosed, but no spedtic examples were made or tested.

Katritzky, et al., J. Chem. Eng. Data 1987, 32, 479–481 prepared certain pyrazinyl compounds of this invention for evaluation as herbicides. There is no teaching that these compounds would be active as fungicides.

SUMMARY OF THE INVENTION

A class of novel heterocyclicacetonitriles which is useful in the control of fungi, especially those with bitunicate asci and uritunicate asci, has been discovered. These compounds are of the general formula:

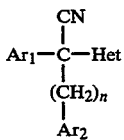

(I)

wherein $Ar_1$ is a substituted or unsubstituted aryl group; $Ar_2$ is a substituted or unsubstituted aryl group or thiopheneyl or furanyl group; Het is a six-membered nitrogen-containing heterocyclic ring; n is the integer 2 or 3; and the agronomically acceptable enantiomorphs, acid addition salts and metal complexes thereof.

This invention also teaches methods of preparing this new class of compounds as well as methods of using the compounds as fungicides.

DETAILED DESCRIPTION OF THE INVENTION

This invention relates to fungicidal compounds of the general formula I wherein $Ar_1$ is selected from an optionally substituted $C_6$ to $C_{10}$ aryl group with up to three substituents independently selected from the group consisting of halogen, nitro, cyano, ($C_1$-$C_{12}$) alkyl, ($C_1$-$C_{12}$) haloalkyl, ($C_3$-$C_8$) cycloalkyl, ($C_5$-$C_8$) cycloalkenyl, ($C_2$-$C_{12}$) alkenyl, ($C_2$-$C_{12}$) alkynyl, ($C_1$-$C_{12}$) alkoxy, ($C_1$-$C_{12}$) haloalkoxy, ($C_1$-$C_{12}$) alkylthio, ($C_1$-$C_{12}$) alkylsulfinyl, ($C_1$-$C_{12}$) alkylsulfonyl, phenyl, phenoxy, phen($C_1$-$C_{12}$)alkyl, phen($C_2$-$C_{12}$)alkenyl, phen($C_2$-$C_{12}$)alkynyl and ($C_5$-$C_6$)cycloalkyl ($C_1$-$C_6$)alkyl; $Ar_2$ is an optionally substituted ($C_6$-$C_{10}$) aryl group wherein the substituents are independently selected from the substituents enumerated above for $Ar_1$; or $Ar_2$ may be thiopheneyl or furanyl; Het is a six membered heterocyclic ring consisting of 3 to 5 carbon atoms and 1 to 3 nitrogen atoms; n is the integer 1, 2 or 3; and the agronomically acceptable enantiomorphs, acid addition salts and metal complexes thereof; and with the proviso that when Het is pyrazinyl and n is two then $Ar_1$ and $Ar_2$ cannot both be phenyl.

Compounds possessing substantially the same properties as the unsubstituted phenyl and phenoxy substituents defined by the formula above, which can be prepared in the same manner and are equivalents thereof are those wherein the phenyl or phenoxy group bears one or more simple substituents, including but not limited to, lower alkyl, halogen and lower alkoxy.

The term "aryl" as used in the present specification and claims means an aromatic ring structure of 6 to 10 carbon atoms, preferably a phenyl or naphthyl group which may be unsubstituted or optionally substituted with up to three substituents, preferably with one substituent, selected from the group consisting of halogen, nitro, cyano, ($C_1$-$C_{12}$) alkyl, ($C_3$-$C_8$) cycloalkyl, ($C_1$-$C_{12}$) haloalkyl, ($C_1$-$C_{12}$) alkoxy, ($C_2$-$C_{12}$) alkenyl, ($C_3$-$C_8$) cycloalkenyl, ($C_2$-$C_{12}$) alkynyl, ($C_1$-$C_{12}$) alkylthio, ($C_1$-$C_{12}$) alkylsulfinyl, ($C_2$-$C_{12}$) alkylsulfonyl, phenyl, phen ($C_1$-$C_{12}$) alkyl, phen ($C_2$-$C_{12}$) alkenyl, phen ($C_2$-$C_{12}$) alkynyl and ($C_5$-$C_6$) cycloalkyl ($C_1$-$C_6$) alkyl.

Typical aryl groups encompassed by this invention are phenyl, naphthyl, 2, 4-dichlorophenyl, 4-methylphenyl, 4-methoxyphenyl, 4-nitrophenyl, 4-fluorophenyl, 4-chlorophenyl, 4-trifluoromethylphenyl, 4-bromophenyl, 3-chlorophenyl, 3-fluorophenyl, 4-bromophenyl, 4-biphenyl, 2-fluorophenyl, 2-chlorophenyl, 2-cyanonaphthyl, 4-chloronaphthyl and 4-methylthiophenyl, 4-phenoxyphenyl, and 4-(2',4'-dichlorophenoxy)phenyl.

By the term "Het" as used in the present specification and claims means a six-membered heterocyclic ring consisting of three to five carbon atoms and one to three nitrogen atoms. Examples of heterocyclic rings encompassed by this invention are 2-pyridyl, 3-pyridyl, 4-pyridyl, 3-pyridyl N-oxide, 2-pyrimidyl, 4-pyrimidyl, 5-pyrimidyl, pyrazinyl, 3-pytidazinyl, 4-pyridazinyl and ttiazenyl.

The term "alkyl" as used in defining the substituents on the aromatic groups in the present specification and claims means both straight and branched carbon chains from one to twelve atoms.

The term "pesticidally or fungicidally effective amount" means a quantity of compound which causes a reduction of the pest or fungus population or decreases crop damage as compared to a control group.

The term "agronomicaily acceptable carrier" means a solid or liquid which is biologically, chemically, and physically compatible with the compounds of this invention.

A preferred embodiment of this invention is the compounds, salts and enantiomorphs represented by formula I wherein $Ar_1$ and $Ar_2$ are independently selected from phenyl or phenyl substituted with up to two substituents selected from the group consisting of methyl, halomethyl, trihalomethyl halogen, and alkoxy; and Het is a six membered heterocyclic ring consisting of 4 or five carbon atoms and 1 or 2 nitrogen atoms; n is the integer 2 or 3; and agronomically acceptable enantiomorphs and add salts thereof.

A more preferred embodiment of this invention is the compounds, salts and enantiomorphs represented by formula I wherein Ar₁ is unsubstituted phenyl, or 2- or 4-halosubstituted phenyl; Ar₂ is unsubstituted phenyl or 3- or 4-halosubstituted phenyl; Het is pyrazinyl, 3-pyridyl or 5-pyrimidyl and n is the integer 2.

A still more preferred embodiment of this invention is the compounds salts and enantiomorphs of formula I wherein Ar₁ is 2-or 4-chloro- or fluorophenyl; Ar₂ is 4-chloro- or 4-fluorophenyl; Het is 3-pyridyl or 5-pyrimidyl; and n is the integer 2.

In another aspect, this invention relates to fungicidal compositions comprising a fungicidally effective amount of the compounds, enantiomorphs, acid addition salts and metal complexes of formula I as described above and an agronomically acceptable inert carrier.

In yet another aspect, this invention relates to a method of controlling fungi comprising contacting said fungi or the locus of said fungi with a fungicidally effective amount of a compound of formula (Ia) as described below:

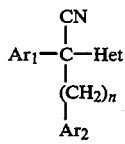
(Ia)

wherein Ar₁ is selected from an optionally substituted C₆ to C₁₀ aryl group with up to three substituents independently selected from the group consisting of halogen, nitro, cyano, (C₁-C₁₂) alkyl, (C₁-C₁₂) haloalkyl, (C₃-C₈) cycloalkyl, (C₅-C₈) cycloalkenyl, (C₂-C₁₂) alkenyl, (C₂-C₁₂) alkynyl, (C₁-C₁₂) alkoxy, (C₁-C₁₂) haloalkoxy, (C₁-C₁₂) alkylthio, (C₁-C₁₂) alkylsulfinyl, (C₁-C₁₂) alkylsulfonyl, phenyl, phenoxy, phen(C₁-C₁₂)alkyl, phen(C₂-C₁₂)alkenyl, phen(C₂-C₁₂)alkynyl and (C₅-C₆)cycloalkyl (C₁-C₆)alkyl; Ar₂ is an optionally substituted (C₆-C₁₀) aryl group wherein the substituents are independently selected from the substituents enumerated above for Ar₁; or Ar₂ may be thiophenyl or furanyl; Het is a six-membered nitrogen-containing heterocyclic ring; n is the integer 1, 2 or 3; and the agronomically acceptable enantiomorphs, acid addition salts and metal complexes thereof.

Compounds encompassed by the present invention include those illustrated in Table I.

The heterocyclicacetonitriles of the present invention may be prepared by standard synthetic routes including the following preferred procedures.

Synthesis Scheme - Route 1

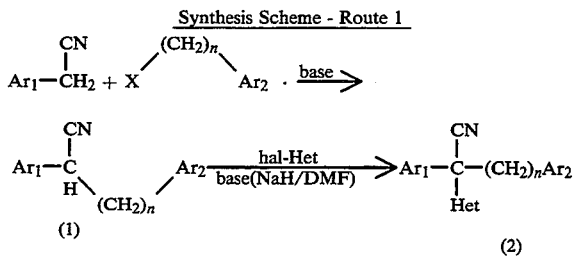

Ar₁, Ar₂, Het and n are as defined above; X is chloro, bromo, methane sulfonate or p-toluene sulfonate.

Route 1 involves preparation of an alkylated benzylcyanide by conventional techniques, (See U.S. Pat. No.4,366,165) then incorporation of the heterocycle via alkylation with the chloro or bromoheterocycle, e.g., 3-bromopyridine or 5-bromopyrimidine. This route is chosen when the side chain is phenethyl, phenpropyl. The heterocydes used in route 1 include 3-pyridyl, 4-pyridyl, 5-pyrimidinyl and pyrazinyl as the halo-heterocyde. However, with benzyl side chains, route 1 is sensitive to the heterocycle employed. With benzyl side chains reaction with 3-bromopyridine restfits in loss of hydrocyanic add and produces pyridyl ethylenes rather than the cyano product. With 5-bromopyrimidine the product can be either the cyano product or the pyrimidinyl ethylene depending on the time and temperature of the reaction.

The first step of route 1 may be conducted under phase transfer conditions by alkylation of the appropriately substituted benzylcyanides with about 1 to 2 equivalents of the appropriate phenylalkylhalide or mesylate or tosylate in the presence of a strong base such as sodium or potassium hydroxide and a catalyst such as tetrabutylamonium bromide with or without a solvent, preferably with a solvent such as toluene or chlorobenzene or a mixture thereof at temperatures of about 0° C. to 100° C., preferably about 10° C. to 40° C.

Alternatively, the first step of route 1 may be conducted by alkylation of the appropriately substituted benzylcyanides using 1 or 2 equivalents of arylalkylhalide in the presence of a strong base such as a metal hydroxide or hydride, e.g., sodium or potassium hydroxide or hydride using dimethylformamide (DMF) or DMF/toluene or dimethylsulfoxide (DMSO) or DMSO/toluene as the solvent at temperatures of about 0° C. to 100° C., preferably about 10° C. to 40° C.

TABLE I

| Cpnd. | Het | Ar₁ | Ar₂ | n |
|---|---|---|---|---|
| A | 5-Triazenyl | 4-Octylphenyl | 4-Trifluoromethylphenyl | 3 |
| B | 5-Pyrimidyl | 2-Ethoxynaphthyl | 4-Allylphenyl | 2 |
| C | 3-Pyridazinyl | 1-Propargylnaphthyl-2 | 3-Propylthiophenyl | 3 |
| D | 4-Pyriadazinyl | 3-Dodecylphenyl | 2-Cyclohexylphenyl | 2 |
| E | 4-Pyridyl | 4-chloro-2-methoxyphenyl | 2-Cyano-3-Nitrophenyl | 3 |
| F | 2-Pyrimidyl | 3-Propylsulfinylphenyl | 3-Phenethylphenyl | 2 |
| G | 5-Pyrimidyl | 4-(3'-Phenylbutene-2')-Phenyl | 3-Methylsulfonylphenyl | 2 |
| H | Pyrazinyl | 2,4-Dinitrophenyl | 3-Cyanophenyl | 2 |
| I | 2-Pyridyl | 2,3,4-Tribromophenyl | 3-Nitro-4-Cyanophenyl | 3 |
| J | 3-Pyridyl | 3-(5'-phenylpentyne-1')-Phenyl | 4-Cyclohexylmethylphenyl | 3 |
| K | 4-Pyrimidyl | 2-Chloro-5-Nitrophenyl | 1-Cyanonaphthyl-2 | 2 |
| L | 5-Pyrimidyl | 4-Phenoxyphenyl | 4-biphenyl | 2 |
| M | 3-Pyridyl | 4-(2',4'-Dichlorophenoxy)phenyl | 4-Trifluoromethoxyphenyl | 3 |
| N | Pyrazinyl | 4-(4'Chlorophenyl)phenyl | 4-Ethoxyphenyl | 2 |

The second step of Route 1 uses about 1.5 equivalents of a strong base such as sodium or potassium hydroxide or sodium or lithium amide or sodium or potassium hydride in a solvent such as DMF or DMSO and the appropriate halo substituted heterocyde at temperatures of about 0° to 100° C., preferably about 75°-80° C. Route 1 is preferred for pyrimidine compounds.

Reaction progress may be monitored by standard analytical procedures such as gas-liquid chromotography. The reactions are typically complete in about 1-6 hours.

Route 1 has been used in the literature for the reaction of diphenylacetonitrile with 3-bromopyridine and 5-bromopyrimidine via sodium amide in liquid ammonia; see U.S. Pat. No. 3,818,009.

Route 1 is further illustrated in Examples 1, 2, 7 and 8.

Synthesis Scheme - Route 2

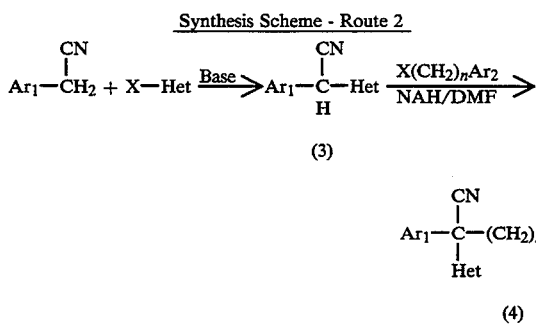

$Ar_1$, $Ar_2$, Het and n rare as defined above; X is chloro or bromo.

Route 2 incorporates the heterocycle during the initial step of the synthesis and allows a convenient method for preparation of analogs. In the literature substituted benzyl cyanides have been reacted with 3-bromopyridine and chloropyrazine. See Katritzky, et al., supra. Preparation using 3-bromopyridine have shown that powdered potassium hydroxide in dimethyl sulfoxide and a 2 fold excess of 3-bromopyridine gives the initial alkylated intermediate 3 in moderate yields. It is preferred to add the base to the nitrile and pyridine in contrast to preforming the anion. These distilled intermediates were coupled via a metal hydride or amide base, preferably sodium in dimethylformamide with phenethyl and phenpropyl bromides. Benzyl chlorides react rapidly and this is the method of choice to prepare the benzyl side chains espedally when the heterocyde is 3-pyridyl. For phenethyl and phenpropyl side chains the chloride, bromide or mesylate may serve as the leaving group; bromide is preferred. In addition, the best results are obtained when the base such as sodium hydride (NaH) is added to the α-aryl pyridylacetonitrile intermediate and alkylating reagent, or the base and alkylating reagent are premixed and the α-phenyl pyridyl acetonitrile is added. This is atypical to most types of alkylation employing NaH.

The N-oxides can be prepared via oxidation for example with m-chloroperbenzoic add (MCPBA) in methylene chloride at 0° to 25° C.

Route 2 is further illustrated in Examples 3 and 4. Table II shows the route of preparation and physical properties of a number of heterocyclic acetonitriles which exemplify this invention.

TABLE II

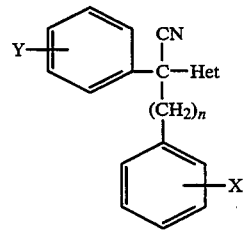

| Number | Y | X | Het | n | mp °C. | Route |
|---|---|---|---|---|---|---|
| 1 | H | 4-Cl | Pyridyl-3 | 2 | 83-84 | 1 |
| 2 | H | 4-Cl | Pyrimidyl-5 | 2 | 89-91 | 1 |
| 3 | H | 4-Cl | Pyrimidyl-5 | 1 | 99-101 | 1 |
| 4 | H | H | Pyridyl-3 | 2 | 70-73 | 1 |
| 5 | H | H | Pyrimidyl-5 | 2 | 94-97 | 1 |
| 6 | H | H | Pyrazinyl | 2 | 90-93 | 1 |
| 7 | H | 2,4-Cl$_2$ | Pyrazinyl | 1 | 81-83 | 1 |
| 8 | 3-Cl | 4-F | Pyridyl-3 | 2 | Oil | 1 |
| 9 | 3-CF$_3$ | 4-Cl | Pyridyl-3 | 2 | Oil | 1 |
| 10 | 3-F | 4-Cl | Pyridyl-3 | 2 | Oil | 1 |
| 11 | 4-Cl | 4-Cl | Pyridyl-3 | 2 | Oil | 1 |
| 12 | 2-F | 4-Cl | Pyridyl-3 | 2 | 87-89 | 1 |
| 13 | 2-Cl | 4-F | Pyridyl-3 | 2 | 89-91 | 1 |
| 14 | 2-Cl | 4-F | Pyridyl-4 | 2 | 121-123 | 1 |
| 15 | H | 4-OCH$_3$ | Pyridyl-3 | 2 | 80-82 | 1 |
| 16 | H | 4-Cl | Pyrazinyl | 2 | 99-101 | 1 |
| 17 | H | 4-Cl | Pyridyl-4 | 2 | 98-100 | 1 |
| 18 | 3-F | H | Pyridyl-4 | 1 | 133 | 1 |
| 19 | 4-F | 3-Cl | Pyridyl-4 | 1 | 116-117 | 1 |
| 20 | 3-CF$_3$ | H | Pyridyl-4 | 1 | 118-119 | 1 |
| 21 | 4-F | 4-Cl | Pyridyl-4 | 1 | 130-131 | 1 |
| 22 | H | 4-Cl | Pyridyl-3 | 1 | 109-111 | 2 |
| 23 | H | 4-Cl | Pyridyl-4 | 1 | 89-91 | 2 |
| 24 | H | 4-F | Pyridyl-3 | 1 | 93-95 | 2 |
| 25 | H | 4-CF$_3$ | Pyridyl-3 | 1 | 101-103 | 2 |
| 26 | 2-F | 4-Cl | Pyridyl-3 | 1 | 119-121 | 2 |
| 27 | 2-F | 4-CF$_3$ | Pyridyl-3 | 1 | 98-100 | 2 |
| 28 | 4-F | H | Pyridyl-3 | 2 | Oil | 2 |
| 29 | 4-F | 4-Cl | Pyridyl-3 | 2 | Oil | 2 |
| 30 | 2-F | 4-F | Pyridyl-3 | 2 | 86-88 | 1 |
| 31 | 4-Br | H | Pyridyl-3 | 2 | Oil | 1 |
| 32 | 3-Cl | H | Pyridyl-3 | 2 | Oil | 2 |
| 33 | 3-Cl | 4-Cl | Pyridyl-3 | 2 | 109-111 | 1 |
| 34 | 3-Cl | 2-F | Pyridyl-3 | 2 | 84-86 | 1 |
| 35 | H | 4-F | Pyridyl-3 | 2 | 98-100 | 2 |
| 36 | 2-F | 3-Cl | Pyridyl-3 | 2 | Oil | 2 |
| 37 | H | H | Pyrazinyl | 1 | 71-73 | 2 |
| 38 | H | 4-Cl | Pyrazinyl | 1 | 98-100 | 2 |
| 39 | H | H | Pyridyl-3 | 1 | 136-138 | 2 |
| 40 | H | H | Pyrimidyl-5 | 1 | 136-138 | 2 |
| 41 | 2-F | 4-Cl | Pyrimidyl-5 | 2 | 86-88 | 1 |
| 42 | 2-F | 4-Cl | Pyrazinyl | 2 | 58-60 | 1 |
| 43 | H | 3-F | Pyridyl-3 | 2 | 83-85 | 2 |
| 44* | H | 4-Cl | Pyridyl-3 | 2 | 169-171 | 2 |
| 45** | H | 4-Cl | Pyridyl-3 | 2 | 116-118 | 2 |
| 46 | H | 3-Br | Pyridyl-3 | 2 | 95-97 | 2 |
| 48 | 2-Cl | 4-Cl | Pyrimidyl-5 | 2 | 122-123 | 1 |
| 49 | 2-F | 4-F | Pyrimidyl-5 | 2 | 88-90 | 1 |
| 50 | 2Cl | 4-F | Pyrimidyl-5 | 2 | 110-112 | 1 |
| 51 | 2-Cl | 4-Cl | Pyrazinyl | 2 | 101-103 | 1 |
| 52 | 2-F | 4-F | Pyrazinyl | 2 | 92-94 | 1 |
| 53 | 2-Cl | 4-F | Pyrazinyl | 2 | 108-110 | 1 |
| 54 | 2-Cl | 4-Cl | Pyridyl-3 | 2 | 90-92 | 1 |
| 55 | 2-OCH$_3$ | 4-Br | Pyrimidyl-5 | 2 | 117-118 | 1 |
| 56 | 2-OCH$_3$ | 4-F | Pyrimidyl-5 | 2 | 102-104 | 1 |
| 57 | H | 4-Phenyl | Pyridinyl-5 | 2 | Oil | 2 |
| 59 | H | 4-CH$_3$ | Pyridyl-3 | 2 | Oil | 1 |
| 60 | H | 4-CH$_3$ | Pyrimidyl-5 | 2 | 67-79 | 1 |
| 61 | H | 4-Cl | Pyridyl-3 | 3 | Oil | 1 |
| 62 | H | 4-Cl | Pyrimidyl-5 | 3 | Oil | 1 |
| 63 | H | 4-Cl | Pyrazinyl | 3 | Oil | 1 |
| 67 | H | 4-Phenyl | Pyrimidyl-5 | 1 | Oil | 1 |
| 68 | H | 4-Phenyl | Pyrazinyl | 1 | Oil | 1 |

*nitrate salt of compound 1
**sulfate salt of compound 1

The heterocyclic acetonitriles, enantiomorphs, add addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Co., Ridgewood, N.J.

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent with permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range from about 20% to about 98%, preferably from about 40% to about 75%.

A water dispersible granular product may be obtained by granulating or agglomerating a suitable wettable powder formulation that is compatible with the active ingredients. Agglomeration may be carried out by any convention method such as pan agglomeration. Illustrative water dispersible granules are described in U.S. Pat. No. 3,954,439.

Dusts are prepared by mixing the heterocyclic acetonitriles, enantiomorphs, salts and complexes thereof with finely divided inert solids which can be organic or inorganic in nature. Materials useful for this purpose include botanical flours, silicas, silicates, carbonates and days. On convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The heterocyclic acetonitriles, enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soft or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention include:

(a) dithiocarbamate and derivatives such as:
ferbam, ziram, maneb, mancozeb,zineb, propineb, metham, thiram, the complex of zineb and polyethylene thiuram disulfide, dazomet, and mixtures of these with copper salts;

(b) nitrophenol derivatives such as:
dinocap, binapacryl, and 2-sec-butyl-4,6-dinitrophenyl isopropyl carbonate;

(c) heterocyclic structures such as:
captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenasimol, bis-(p-chlorophenyl)-3-pyridinemethanol, bis-(p-chlorophenyl)-5-pyrimidinemethanol, triarimol,flutriafol, flusilazole, propiconazole, etaconazole, myclobutanil, alpha-[2-(4-chlorophenyl)ethyl]-alpha-phenyl-1H-1,2,4-triazole-1-propanenitrile, hexaconazole, cyproconazole, terbuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxardlido-6-methyl-1,4-oxathiin, cis- N-[(1,1,2,2-tetrachloroethyl)thiol ]-4-cyclohexene- 1,2-dicarboximide, cydoheximide, dehydroacetic add, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-B,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo- 1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as:
chloranil, dichlone, chloroneb, tricamba, TCPN, dichloran, 2-chloro-l-nitropropane, polychloronitrobenzenes such as pentachloronitrobenzene (PCNB), and tetrafluorodichloroacetone;

(e) fungicidal antibiotics such as:
griseofulvin, kasugamycin, polyoxin, validamycin, and streptomycin;

(f) copper-based fungicides such as:

copper hydroxide, cuprous oxide, basic cupric chloride, basic copper carbonate, copper terephthalate, copper naphthenate and Bordeaux mixture; and (g) miscellaneous fungicides such as:

dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricydazole.

The heterocydicacetonitriles enantiomorphs, acid addition salts and metal salt complexes of this invention can be advantageously employed in various ways. Since these compounds possess broad spectrum fungicidal activity, they can be employed in the storage of cereal grain. These complexes can also be employed as fungicides in turf, fruit and nut orchards, vegetables and golf course applications. Other applications of the compounds of this invention will suggest themselves to those skilled in the art of agriculture and horticulture.

The compounds of the present invention have fungitoxic activity, providing control of a broad spectrum of phytopathogenic fungi including those in the classes of Deuteromycetes (Fungi Imperfecti), Oomycetes, Basidiomycetes and Ascomycetes. More particularly, the method of this invention provides for control of organisms which cause diseases on many crops including such important genera as Erysiphe, Pucdnia, Leptoshaeria, Thanatephorus, Pyricularia, Phytophthora, Plasmopara, Alternaria, Guignardia, Pseudocercosporella, Venturia, Monilinia, and Ustilago. More particularly, wheat diseases including powdery mildew (*Erysiphe graminis*), leaf rust (*Puccinia recondita*), stem rust (*Puccinia graminis* f. sp. *tritid*) and septoria leaf and glume blotch (*Leptoshaeria nodorum*) are controlled by the method of the invention. Other diseases controlled include cercospora leaf spots (*Mycosphaerella arachidis* and *Cercospora beticola*), botrytis diseases (*Botryotinia fuckelioniana*), helminthosporium diseases (*Cochliobolous moiyabeanus, Cochliobolous sativus, Cochliobolus heterostrophus*), rice blast (*Magnaporthe grisea*) and alternaria blight (*Alternaria solani*). Consequently, various comopunds of this invention may be useful in treating fungi which may affect cereal, fruit, nut, vegetable, feed and fiber crops.

The following examples are provided merely as illustrations and are not to be considered as limitations or restrictions of the scope of this invention which is defined by the claims.

EXAMPLE 1

Preparation of 4-(4-chlorophenyl)-2-phenyl-2-(3-pyridyl)-butanenitrile (compound 1)

In a 1 liter 3 neck round bottomed flask, under $N_2$, was charged 7.2 g of 60% NaH (1.5 eq., 0.15 moles), washed 2 times with 25 ml. hexanes in 100 mi. dimethylformamide (DMF). To the base was added dropwise 25.5 g of 4-(4-chlorophenyl)-2-phenylbutanenitrile (1.0 eq., 0.10 moles) in 150 ml. DMF and was stirred for 45 min. at rt. This was followed by the addition of 14.2 g of 3-bromopyridine (0.9 eq., 0.09 moles) in 75 ml. of DMF. The mixture was then heated at 75°-80° C. for 5 hrs. at which time gas-liquid GLC analysis indicated no unreacted 3-bromo pyridine remained. The reaction was quenched by the addition of 200 ml. of $H_2O$ and then extracted with 400 ml. of 1:1 EtOAc:Et$_2$O. The ethyl acetate/ether phase was washed with 250 ml. water ($H_2O$) and 400 ml. of 10% hydrochloric acid (HCl), dried over magnesium sulfate (MgSO$_4$) and concentrated to give 29.1 g of oil. This crude product was further purified via an acid/base extraction. The crude product was dissolved in 300 ml. of toluene to which 300 ml. of 25% sulfuric acid ($H_2SO_4$) was added which resulted in separation of an oil. To the oil and add was added 300 ml of ethyl acetate (EtOAc) which was neutralized with 50% sodium hydroxide (NaOH) to a pH of 10. This was washed with $H_2O$ (2×300 ml.), dried and concentrated to give 18.2 g of oil which solidified. Trituration with 40 ml. of isopropanol gave 13.0 g of a white solid, mp 83°–84° C. (43.4% yield).

| $C_{21}H_{17}N_2Cl$ | C | H | N | Cl |
| --- | --- | --- | --- | --- |
| Theor: | 75.79 | 5.11 | 8.42 | 10.68 |
| Found: | 74.69 | 5.22 | 8.24 | 11.14 |

NMR (60 MHz): 2.6–2.8(s, 4H), 7.0–7.5(m, 10H), 7.6–7.8(m, 1H), and 8.5–8.8(m, 2H).

EXAMPLE 2

Preparation of 4-(4-chlorophenyl)-2-phenyl-2-(5-pyrimidinyl)-butanenitrile (Compound 2)

In a 250 ml. 3 neck round bottomed flask under nitrogen was charged 1.2 g of 60% NaH (1.5 eq., 0.0293 moles), washed 2 times with 15 ml. hexanes, in 40 ml. DMF. Dropwise was added 5.0 g. of 4-(4-chlorophenyl)-2-phenylbutanenitrile (1.0 eq., 0.0195 moles) in 10 ml. of DMF and was stirred for one hour at rt. This was followed by the addition of 4.67 g. of 5-bromopyrimidine (1.5 eq., 0.0293 moles) in 10 ml. of DMF to the reaction mixture which resulted in an exotherm to 35° C. After 45 min. GLC analysis showed no unreacted nitrile. The reaction was quenched by the addition of 100 ml. Water and then extracted with 250 ml. EtOAc. The organic phase was washed with 2 times 100 ml. water, dried over MgSO$_4$ and concentrated to give 7.3 g. of oil. 6.0 g. of crude product was purified by flash chromatography with 3:7 EtOAc/hexane to give 2.3 g. of a white solid mp. 89°–91° C. (43.1% based on chromatographic portion).

| $C_{20}H_{16}N_3Cl$ | C | H | N | Cl |
| --- | --- | --- | --- | --- |
| Theor: | 71.96 | 4.80 | 12.59 | 10.64 |
| Found: | 72.39 | 5.02 | 12.48 | 10.57 |

NMR (200 MHz): 2.6–2.7(s, 4H), (9H), 8.8(s, 2H), and 9.2-(s, 1H).

EXAMPLE 3

Preparation of alpha-4-fluorophenyl-3-pyridylacetonitrile

In a 1 liter 3 neck round bottomed flask was charged 20.0 g. of 4-fluorobenzyl cyanide (1.0 eq., 0.15 moles), in 300 ml. dimethylsulfoxide (DMSO) (dried over molecular sieves), and 46.8 g. of 3-bromopyridine (2.0 eq., 0.30 moles) while stirring under $N_2$. The reaction mixture was heated to 60° C. at which time 12.4 g of KOH (1.5 eq., 0.22 moles) as powdered pellets was added neat.

The reaction exotherms to 80° C. and was monitored by GLC. After 30 min., an additional 2.4 g. of potassium hydroxide (KOH) was added (0.3 eq., 0.043 moles) and 1 hr. later GLC showed 6% unreacted nitrile. The reaction was quenched by the addition of 500 ml. of water and then extracted with 1 liter of ether. The organic phase was washed 3 times 250 ml. $H_2O$, dried over $MgSO_4$ and concentrated to give 50 g. of oil. The crude product was distilled under vacuum to give 15.7 g. of oil (49.4% yield) bp 160°–170° C. @1–2 mm. Hg. NMR (200 MHz): 5.2(s, 1H), 7.0–7.4 (m, 5H), 7.6–7.8 (m, 1H), and 8.5–8.6 (m, 2H).

EXAMPLE 4

Preparation
2-(4-fluorophenyl)-4-phenyl-2-(3-pyridyl)butanenitrile
(Compound 28)

In a 300 ml. 3 neck round bottomed flask under $N_2$ was charged 0.9 g. of 60% NaH (1.5 eq., 0.0225 moles), washed 2 times with 15 ml hexanes, in 40 ml. DMF and 5.5 g. of 2-bromoethylbenzene (2.0 eq., 0.030 moles). This was followed by the addition of 3.18 g. of alpha-4-fluorophenyl-3-pyridylacetonitrile (1.0 eq., 0.015 moles) in 10 ml. DMF which resulted in an exotherm to 46° C. After 15 min. GLC analysis showed no unreacted nitrile. The reaction was quenched by the addition of 100 ml. water and then extracted with 250 ml. ether. The organic phase was washed twice with 100 mi. water, dried over $MgSO_4$ and concentrated to give 5.0 g. of oil. The crude product was purified by flash chromatography with 2:3 EtOAc/hexane to give 3.7 g. of an oil (78.0 % yield).

| $C_{21}H_{17}N_2F$ | C | H | N | F |
| --- | --- | --- | --- | --- |
| Theor: | 79.75 | 5.38 | 8.86 | 6.41 |
| Found: | 78.50 | 5.18 | 8.54 | 6.09 |

NMR (200 MHz): 2.6–2.8(s,4H), 7.0–7.5(m, 10H), 7.7–7.8(m, 1H), and 8.5–8.7(m, 2H).

EXAMPLE 5

Preparation of 4-chlorophenethyl bromide

A 500 ml. 3 neck round bottomed flask under nitrogen was charged 15.65 g. of 4-chlorophenethanol (1.0 eq., 0.10 moles) in 60 ml. toluene. To the reaction was added dropwise 41.6 g of thionyl bromide (2.0 eq., 0.20 moles) in 15 ml. of toluene maintaining the temp. below 25 C. Finally, 8.7 g. pyridine (1.1 eq., 0.11 moles) in 20 ml. toluene was added dropwise again keeping the temperature below 30° C. with an external ice bath. The reaction was monitored by GLC and after 1 hr. an additional 14.0 g of thionyl bromide (0.67 eq. 0.067 moles) was added followed three hours later by 9.7 gms. (1.1 eq., 0.11 moles). Subsequently 4.3 g. of pyridine was added (0.55 eq., 0.055 moles) after which GLC indicated all the alcohol was consumed. The reaction was quenched by the addition of 300 ml of water while cooling with an ice bath after which 400 ml. of ether was added. The ether was washed water three times with 250 ml.), dried over $MgSO_4$ and concentrated to give 14.4 g of product as an oil (65.2% yield). NMR (60 MHz): 2.9–3.7 (m, 4H) and 7.0–7.4 (ABq, 4H).

EXAMPLE 6

Preparation of
4-(4-chlorophenyl)-2-(2-fluorophenyl)-butanenitrile

To a 5 L 4-neck round bottomed flask under a nitrogen atmosphere was charged 93.4 g., 60% sodium hydride (1.05 equiv., 2.33 moles) this mixture was washed with hexane, and then added 340 ml. DMF was added. Then 300 g. of 2-fluorophenylacetonitrite (1.0 equiv. 2.22 moles) was added dropwise maintaining solution temperature at 30° C. with an ice bath. After stirring for one hour 250 ml., toluene was added to the reaction mixture followed by dropwise addition in 3 equal portions, 532 g. 4-chlorophenethyl mesylate (1.02 equiv. 2.27 moles) in 340 ml. toluene/340 ml. DMF solution. The reaction solution temperature was maintained <30° C. during the 1.5 hour addition. 250 ml. of toluene was added to the reaction after each of the three portions of mesylate was added to avoid solidification. Reaction progress was monitored by GLC analysis. After stirring 3 hours, the reaction solution was poured into 3 L of 2% HCl solution. The phases were separated and the aqueous phase further extracted with two times one liter portion of ether. The organic extractions were combined and washed with two times with one liter of of water followed by 1 L of brine, dried over anhydrous magnesium suifate, filtered and concentrated in vacuo to give 596 g. oil. The oil was distilled at 150° C. (0.1 mm Hg.) to give 305.2 g. oil (50.3%) NMR (200 MHz): 2.1–2.3 (m, 2H), 2.7–2.9 (m, 2H), 4.0–4.1 (t, 1H), 7.0–7.5 (m, 8H).

EXAMPLE

Preparation of
4-(4-chlorophenyl)-2-(2-fluorophenyl)-2-(3-pyridyl)-butanitrile (Compound 26)

A 5 L 4-neck round bottomed flask was charged under a nitrogen atmosphere with 104 grams of 60% sodium hydride (1.3 equiv. 2.6 moles), washed with hexanes, and then 1 L of DMF was added. To this mixture was added dropwise 547 grams 4-(4-chlorophenyl)-2-(2-fluorophenyl)-butanenitrile (1.0 equiv., 2.0 moles) in 600 ml. DMF causing an exotherm to 41° C. The reaction mixture was stirred for one hour after which 348 grams 3-bromopyridine (1.1 equiv., 2.2 moles) in 400 ml. DMF. was added dropwise to the reaction mixture. The reaction was heated at 70° C. and progress monitored by GLC analysis. Mter 12 hours, 20 g. more of 3-bromopyridine (0.13 moles) was added and heated at 70° C. for 4 hours. After cooling to ambient, temperature, the reaction solution was poured into 7 L of water and extracted with 1.5 L of ethyl acetate. The aqueous phase was then extracted further with 2×1 L ethyl acetate/ether 1:1 solutions. The extractions were combined and washed with 2×1 L water portions followed by a 500 ml. brine wash. The organic phase was dried over anhydrous magnesium sulfate, filtered, treated with charcoal, filtered through celite, and concentrated in vacuo. The oil was dissolved in a minimal amount of ether to which hexane was added until the solution was turbid. Solid formed while stirring for 2 days. The solid was filtered and then triturated with hexane/2-propanol to give 317 grams of a tan solid (45.2% yield), m.p. 90°–92° C.
I. R. (nujol): 2220 (C≡N)cm$^{-1}$
NMR (200 MHz): 2.5–3.0 (m, 4H), 7.0–7.5(m, 8H), 7.6–7.8(m, 2H), 8.5–8.7 (m, 2H)

| Elemental Analysis: $C_{21}H_{16}N_2ClF$ | | | | |
|---|---|---|---|---|
| C | H | N | CL | F |
| Theor: 71.90 | 4.56 | 7.99 | 10.13 | 5.42 |
| Found: 71.86 | 4.64 | 7.92 | 10.18 | 5.19 |

EXAMPLE 8

Preparation of 4-(4-chlorophenyl)-2-(2-fluorophenyl)-2-(5-pyrimidyl) butanenitrile (Compound 41)

A 1 L 4-neck flask under a nitrogen atmosphere was charged with 4.4 g. of 60% sodium hydride (1.1 equiv., 0.11 moles), and washed with hexanes, in 75 ml. DMF. Then over 30 minutes, 27.3 g. of 4-(4-chlorophenyl)-2-(2-fluorophenyl) butanenitrile (1.0 equiv., 0.10 moles) in 110 ml. DMF was added dropwise to the base causing an exotherm to 30° C. After the addition was complete, the reaction mixture was stirred for 30 minutes. Over 5 minutes 17.5 g. of 5-bromopyrimidine (1.1 equiv., 0.11 moles) in 75 mi. DMF was added to the reaction mixture which was heated at 50° C. and monitored by GLC analysis. The reaction was quenched after 2 hours by the addition of 350 ml. water and extracted with 600 ml. ethyl acetate. The organic phase was washed with three 300 ml. portions of water, the organic phase dried over anhydrous magnesium sulfate, and then concentrated in vacuo at 50° C. to give 34.2 grams oil which solidified. The solid was with triturated with 75 ml. isopropanol, filtered, and dried to give 16.5 g. white solid (47.0% yield), m.p.=86° C.–88° C.

I.R. (nujol): 2240 (C≡N) cm$^{-1}$
NMR (200 MHZ): 2.6–3.0 (m, 4H), 7.0–7.8 (m, 8H), 8.8 (s, 2H), 9.2 (s, 1H

| Elemental Analysis: $C_{20}H_{15}N_3ClF$ | | | | |
|---|---|---|---|---|
| C | H | N | Cl | F |
| Theor: 68.28 | 4.27 | 11.95 | 10.10 | 5.40 |
| Found: 68.13 | 4.14 | 11.83 | 10.37 | 5.23 |

EXAMPLE 9

Fungicide Test Methods

The compounds of this invention were tested for fungicidal activity in vivo against cucumber downy mildew (CDM), rice blast (RB), tomato early blight (TEB), tomato late blight (TLB), wheat stem rust (WSR), wheat leaf rust (WLR), septoria leaf and glume blotch of wheat (SNW) and wheat powder mildew (WPM).

The compounds were dissolved in a 2:1:1 mixture of water, acetone, and methanol, sprayed onto the plants and allowed to dry the utilized control plants which were sprayed with the water, acetone, and plants were inoculated with the fungus after about 24 hours. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants) at a given compound dosage in parts per million.

Cucumber Downy Mildew (CDM):

Pseudoperonospora cubensis was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml. of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 5 to 6 days in a controlled temperature room at 65° F. to 75° F. Six days after inoculation, the percent disease control was determined.

Rice Blast (RB):

Two week old M201 rice plants were inoculated withh 2.5×10$^5$ sposes per pot of Magnaporthe grisea (Pyricularia oryzae) by spraying the leaves and stems with a DeVilbiss atomizer. The inoculated plants were incubated in a humid environment at 80° F. for about 24 hours, then placed in a greenhouse environment (70° F. to 75° F.). Six to seven days after inoculation, the percent disease control was determined.

Tomato Early Blight (TEB):

Alternaria solani spores were obtained from V-8 juice agar without CaCO$_3$ for inoculation of San Marzano cultivar tomato seedlings grown for about 18 days under greenhouse conditions. Plants were incubated in a mist chamber at 75° F. for 24 hours after inoculation with a DeVilbiss atomizer. Plants were evaluated for disease control four days after inoculation by comparison to standard area diagrams.

Tomato Late Blight (TLB):

Phytophthora infestans was cultured on V8 juice plus CaCO$_3$ agar for three to four weeks. The spores were washed from the agar with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then removed to the controlled environment room (65°–70° F.) and after five days disease control levels were evaluated.

Wheat Leaf Rust (WLR) and Wheat Stem Rust (WSR).

Puccinia recondita f. sp. tritici (Races PKB and PLD) was increased on seven day old wheat (cultivar Fielder) over a 14 day period in the greenhouse. Puccinia graminios F. tritici was increased on Tyler cultivar wheat seedlings in a similar manner. Spores were collected from the leaves with a cyclone vacuum or by settling on aluminum foil (and stored or used fresh). A spore suspension was prepared by adding 20 mg. (urediospores) per. mi. of Soltrol oil. The suspension was dispensed into gelatin capsules (0.7 ml. capacity) which attach to the oil atomizers. One capsule is used per flat of twenty of the two inch square pots of seven day old Fielder wheat. Inoculated plants were placed in a mist cabinet at 68° F. for 24 hours. Disease control levels were evaluated eleven days after inoculation.

Wheat Powdery Mildew (WPM):

*Erysiphe graminis* (f. sp. *tritici*) was cultured on Hart wheat seedlings in a controlled temperature room at 65° F. to 75° F. Mildew spores were shaken from the culture plants onto Hart wheat seedlings which had been sprayed previously with the fungicidal compound. The inoculated seedlings were kept in a controlled temperature room at 65° F. to 75° F. and subirrigated. The percent disease control was rated 8 to 10 days after the inoculation.

Wheat Glume Blotch: *Septoria nodorum*, (SNW):

A. Innoculum Production:

Multiple culture isolates from representative wheat growing areas (for example S74-20A; S76-8 and S80-509 from the University of Georgia, Athens, Ga.) were used in the screen to insulate against failure, avirulence or narrow germ plasm of any one of the isolates. The isolates had a color range from pink to dark gray black on the Czapek-Dox V8 agar.

Pieces of inoculum from the leading edge of the colony from 2 or 3 week old plates were placed on Czapek-Dox V-8 plates.

These were incubated from 48–72 hours in the dark at 20° C. and then placed in growth chambers at 20° C. with alternating light and dark 12 h:12 h for approximately three weeks.

B. Inoculation:

One hundred mls per 10–15 plates of deionized water was poured into one-half gallon jars; then the portion of the plate with the fungal material was excised from the plate and dropped in the jar. Ten to to twenty plates were placed in each jar and shaken vigorously for 15–30 seconds and allowed to stand for 5–10 minutes.

The spore concentration was then filtered with cheesecloth and diluted to the appropriate concentration. Thirty to forty plates make about 1 liter of diluted inoculum. A spore concentration of about $3.0 \times 10^6$ per ml was used.

A water agar spore germination test was conducted with each batch of inoculum. A drop of inoculum was spread over the surface of the plate and allowed to germinate for 24 hrs. The germination percentage was usually between 60–80%.

One week old Fielder wheat plants were used for disease evaluations. Twenty pots per flat were arranged with untreated controls in opposite corners of each flat. One half ($\frac{1}{2}$) the volume of a Devilbis atomizer (about 22 mls) of inoculum was then sprayed on each flat. Each flat was rotated midway through the inoculation to insure uniform distributed conidia on leaves.

The flats were air dried about 10–15 minutes and then placed in cabinets which had a temperature of 20° C., 12 hr:12 hr light/dark and 100% humidity. The wheat plants were incubated in these cabinets for 96 hrs. and then transferred to a Conviron chamber for disease development for 8 days at 20° C. with a daytime humidity of 90% and 95% relative humidity at night.

C. SNW Disease Rating Protocol

Disease assessment was as followsi

The disease was evaluated 10 days following inoculation.

C = no lesions or flecks visible
99 = clear leaf with 1-2 flecks
95 = flecking visible, but no lesions visible
90 = flecking with 1-2 tiny lesions/pot of plants
80 = some leaf tip necrosis, flecking and 1-5 lesions/leaf
50 = lesions with $\frac{1}{4}$ leaf necrosis
0 = abundant lesions with leaf necrosis Table III shows the fungicidal activity of the exemplory compounds.

Table IV gives elemental analysis of selected examples.

TABLE III

| | Fungicidal Activity ppm/% Control | | | | | | | |
|---|---|---|---|---|---|---|---|---|
| Number | CDM | RB | TEB | TLB | WLR | WPM | SNW* | WSR |
| 1 | 100/85 | 200/70 | 100/0 | 100/0 | 100/95 | 100/99 | 100/95 | 100/100 |
| 2 | 0 | 100/90 | 200/88 | 100/0 | 200/95 | 200/99 | 200/95 | — |
| 3 | 100/0 | 100/80 | 100/0 | 100/95 | 100/0 | 100/100 | 100/0 | 100/90 |
| 4 | 100/100 | 100/0 | 100/0 | 100/0 | 100/0 | 100/100 | 100/90 | 100/90 |
| 5 | 100/70 | 100/0 | 100/0 | 100/0 | 100/0 | 100/100 | 400/90 | 100/75 |
| 6 | 100/0 | 100/50 | 100/0 | 100/0 | 100/0 | 100/100 | 100/50 | — |
| 7 | — | 200/50 | 100/0 | 200/85 | 200/0 | 200/100 | 100/0 | 100/50 |
| 8 | 200/95 | 200/0 | — | 200/80 | 200/50 | 100/90 | — | — |
| 9 | 100/70 | 200/0 | 100/0 | 100/0 | 200/80 | 200/100 | 100/50 | 100/100 |
| 10 | 100/70 | 200/0 | 100/0 | 100/0 | 200/80 | 200/99 | 100/80 | 100/90 |
| 11 | 100/70 | 200/0 | 100/0 | 100/0 | 200/0 | 200/95 | — | 100/90 |
| 12 | 200/85 | 200/90 | 100/88 | 200/0 | 200/99 | 200/100 | 200/90 | 100/90 |
| 13 | 200/50 | 200/50 | 100/98 | 200/90 | 200/95 | 200/100 | 200/50 | 100/100 |
| 14 | 200/85 | 200/50 | — | 200/50 | 200/25 | 200/99 | 25/0 | 100/75 |
| 15 | 200/85 | 200/50 | 100/0 | 200/0 | 200/95 | 200/100 | 100/80 | 100/90 |
| 16 | 200/85 | 200/0 | 100/50 | 200/0 | 200/50 | 200/99 | 200/90 | 100/0 |
| 17 | 200/0 | 200/50 | 200/0 | 200/0 | 200/50 | 200/99 | 100/0 | 100/75 |
| 18 | 100/0 | 200/75 | 200/0 | 600/0 | 600/75 | 600/75 | 100/0 | 100/0 |
| 19 | — | 200/0 | 200/0 | 600/100 | 600/0 | 600/75 | — | — |
| 20 | — | 200/90 | 200/0 | 600/0 | 600/50 | 600/75 | — | — |
| 21 | 200/0 | 200/0 | 200/0 | 600/0 | 600/0 | 200/50 | — | — |
| 22 | 200/0 | 200/0 | 200/0 | 200/80 | 200/25 | 200/100 | 200/0 | — |
| 23 | 200/95 | 200/50 | 200/0 | 600/0 | 600/50 | 600/0 | — | — |
| 24 | 200/0 | 200/99 | 200/50 | 200/100 | 200/0 | 200/100 | — | — |
| 25 | 200/0 | 200/75 | 200/0 | 200/80 | 200/25 | 200/95 | — | — |
| 26 | 200/95 | 200/50 | 200/50 | 200/0 | 200/25 | 200/99 | — | — |
| 27 | 200/95 | 200/50 | 200/0 | 200/0 | 200/25 | 200/99 | 100/0 | 100/0 |
| 28 | 200/0 | 200/75 | — | 200/0 | 200/0 | 200/100 | — | — |
| 29 | 200/50 | 200/0 | 100/0 | 200/0 | 200/0 | 200/99 | 200/80 | — |
| 30 | 200/0 | 200/75 | 200/75 | 200/0 | 200/90 | 200/100 | 200/90 | 100/99 |
| 31 | 200/50 | 200/0 | 200/0 | 200/0 | 200/50 | 200/75 | — | — |
| 32 | 200/90 | 200/0 | 200/75 | 200/0 | 200/0 | 200/100 | 100/50 | 100/100 |

TABLE III-continued

| | | | Fungicidal Activity ppm/% Control | | | | | |
|---|---|---|---|---|---|---|---|---|
| Number | CDM | RB | TEB | TLB | WLR | WPM | SNW* | WSR |
| 33 | 200/50 | 200/0 | 200/0 | 200/0 | 200/99 | 200/99 | 100/50 | 100/90 |
| 34 | 200/70 | 200/75 | 200/88 | 200/0 | 200/0 | 200/100 | 100/0 | 100/0 |
| 35 | 200/0 | 200/0 | 200/50 | 200/0 | 200/80 | 200/95 | 200/90 | — |
| 36 | 200/0 | 200/0 | 200/50 | 200/50 | 200/80 | 200/99 | 100/50 | 100/99 |
| 37 | 200/80 | 200/90 | 200/0 | 200/70 | 200/50 | 200/85 | — | — |
| 38 | 200/85 | 200/90 | 200/0 | 200/85 | 200/0 | 200/100 | — | — |
| 39 | 200/95 | 200/75 | 200/0 | 200/85 | 200/50 | 200/100 | — | 100/0 |
| 40 | 200/80 | 200/75 | 200/0 | 200/0 | 200/0 | 200/95 | — | — |
| 41 | 200/0 | 200/0 | 200/98 | 200/0 | 200/90 | 200/99 | 200/95 | 200/99 |
| 42 | 200/95 | 200/0 | 200/0 | 200/85 | 200/90 | 200/99 | 200/95 | — |
| 43 | 200/70 | 200/0 | 200/0 | 200/0 | 200/0 | 200/99 | 200/80 | 200/99 |
| 44 | 200/70 | 200/0 | 200/0 | 200/70 | 200/90 | 200/99 | 200/80 | 200/90 |
| 45 | 200/0 | 200/50 | 200/75 | 200/90 | 200/90 | 200/99 | 200/90 | 200/90 |
| 46 | 200/0 | 200/0 | 200/0 | 200/85 | 200/80 | 200/99 | 200/90 | 200/90 |
| 48 | 200/0 | — | 200/50 | 200/0 | 200/95 | 200/100 | 200/80 | 200/99 |
| 49 | 200/0 | — | 200/50 | 200/0 | 200/90 | 200/100 | 200/90 | 200/99 |
| 50 | 200/0 | — | 200/50 | 200/0 | 200/90 | 200/99 | 200/50 | 200/100 |
| 51 | 200/0 | — | 200/0 | 200/0 | 200/90 | 200/99 | 200/80 | 200/100 |
| 52 | 200/50 | — | 200/0 | 200/0 | 200/50 | 200/99 | 200/50 | 200/99 |
| 53 | 200/0 | — | 200/0 | 200/0 | 200/0 | 200/99 | 200/50 | 200/99 |
| 54 | 200/50 | — | 200/0 | 200/80 | 200/99 | 200/99 | 200/50 | 200/99 |
| 55 | 200/95 | — | 200/90 | 200/0 | 200/75 | 200/95 | 200/80 | — |
| 56 | 200/95 | — | 200/85 | 200/0 | 200/0 | 200/95 | 200/0 | — |
| 57 | 200/0 | — | 200/0 | 200/0 | 200/85 | 200/75 | 200/0 | — |
| 59 | 200/75 | — | 200/0 | 200/0 | 200/75 | 200/100 | 200/90 | — |
| 60 | 200/25 | — | 200/90 | 200/0 | 200/0 | 200/99 | 200/90 | — |
| 61 | 200/50 | — | 200/0 | 200/0 | 200/0 | 200/90 | 200/50 | — |
| 62 | 200/50 | — | 200/0 | 200/0 | 200/0 | 200/90 | 200/80 | — |
| 63 | 200/0 | — | 200/75 | 200/0 | 200/50 | 200/95 | 200/0 | — |
| 67 | 200/85 | — | 200/0 | 200/0 | 200/0 | 200/85 | 200/0 | — |
| 68 | 200/50 | — | 200/0 | 200/0 | 200/0 | 200/90 | 200/0 | — |

*See Example 9 for SNW rating scale.

TABLE IV

| Cmpd. No. | Empirical Formula | Elemental Analyses Calcd./Found | | | | | |
|---|---|---|---|---|---|---|---|
| | | C | H | N | Cl | F | Br |
| 8 | $C_{21}H_{16}N_2ClF$ | 71.90 | 4.56 | 7.99 | 10.13 | 5.42 | |
| | | 69.94 | 4.45 | 7.62 | 11.47 | 5.27 | |
| 9 | $C_{22}H_{16}N_2ClF_3$ | 65.92 | 4.00 | 6.99 | 8.86 | 14.23 | |
| | | 64.75 | 3.75 | 6.73 | 9.51 | 14.08 | |
| 10 | $C_{21}H_{16}N_2ClF$ | 71.90 | 4.56 | 7.99 | 10.13 | 5.42 | |
| | | 69.42 | 4.07 | 7.16 | 12.73 | 4.59 | |
| 11 | $C_{21}H_{16}N_2Cl_2$ | 68.66 | 4.36 | 7.63 | 19.35 | | |
| | | 68.67 | 4.52 | 7.92 | 19.02 | | |
| 29 | $C_{21}H_{16}N_2ClF$ | 71.90 | 4.56 | 7.99 | 10.13 | 5.42 | |
| | | 70.90 | 4.20 | 7.54 | 9.81 | 5.04 | |
| 31 | $C_{21}H_{17}N_2Br$ | 66.84 | 4.51 | 7.43 | | | 21.22 |
| | | 67.80 | 4.52 | 6.87 | | | 20.68 |
| 32 | $C_{21}H_{17}N_2Cl$ | 75.81 | 5.11 | 8.42 | 10.65 | | |
| | | 74.03 | 5.47 | 8.47 | 10.33 | | |
| 36 | $C_{12}H_{16}N_2ClF$ | 71.90 | 4.56 | 7.99 | 10.13 | 5.42 | |
| | | 71.22 | 4.60 | 7.97 | 10.59 | 5.78 | |
| 57 | $C_{27}H_{22}N_2$ | 86.63 | 5.88 | 7.49 | | | |
| | | 84.37 | 5.82 | 6.94 | | | |
| 59 | $C_{22}H_{20}N_2$ | 84.62 | 6.41 | 8.97 | | | |
| | | 84.20 | 6.48 | 8.95 | | | |
| 61 | $C_{22}H_{19}N_2Cl$ | 76.19 | 5.48 | 8.08 | 10.24 | | |
| | | 75.68 | 5.60 | 7.86 | 10.61 | | |
| 62 | $C_{21}H_{18}N_3Cl$ | 72.52 | 5.18 | 12.09 | 10.21 | | |
| | | 72.05 | 5.24 | 12.06 | 10.78 | | |
| 63 | $C_{21}H_{18}N_3Cl$ | 72.52 | 5.18 | 12.09 | 10.21 | | |
| | | 72.10 | 5.10 | 11.99 | 10.96 | | |

Although the invention has been described with regard to its preferred embodiments, which constitute the best mode presently known to the inventors, it should be understood that various changes and modifications as would be obvious to one having ordinary skill in this art may be made without departing from the scope of the invention, which is set forth in the following claims.

We claim:

1. A compound of the formula:

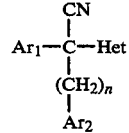

wherein $Ar_1$ is selected from an optionally substituted $C_6$ to $C_{10}$ aryl group with up to three substituents independently selected from the group consisting of halogen, nitro, cyano, $(C_1-C_{12})$ alkyl, $(C_1-C_{12})$ haloalkyl, $(C_3-C_8)$ cycloalkyl, $(C_5-C_8)$ cycloalkenyl, $(C_2-C_{12})$ alkenyl, $(C_2-C_{12})$ alkynyl, $(C_1-C_{12})$ alkoxy, $(C_1-C_{12})$ haloalkoxy, $(C_1-C_{12})$ alkylthio, $(C_1-C_{12})$ alkylsulfinyl, $(C_1-C_{12})$ alkylsulfonyl, phenyl, phenoxy, phen$(C_1-C_{12})$alkyl, phen$(C_2-C_{12})$alkenyl, phen$(C_2-C_{12})$alkynyl and $(C_5-C_6)$cycloalkyl $(C_1-C_6)$alkyl; $Ar_2$ is an optionally substituted $(C_6-C_{10})$ aryl group wherein the substituents are independently selected from the substituents enumerated above for $Ar_1$; or $Ar_2$ may be thiopheneyl or furanyl; Het is a pyridyl ring; n is the integer 2 or 3; and the agronomically acceptable enantiomorphs, acid addition salts and metal complexes thereof.

2. The compound of to claim 1 wherein $Ar_1$ and $Ar_2$ are independently selected from phenyl or phenyl substituted with up to two substituents selected from the group consisting of methyl, halomethyl, halogen, and alkoxy; and Het is a pyridyl ring; n is the integer 2 or 3; and agronomically acceptable enantiomorphs and acid salts thereof.

3. The compound of claim 1 wherein $Ar_1$ is phenyl or 2- or 4-halosubstituted phenyl; $Ar_2$ is phenyl or 3- or 4-halosubstituted phenyl; Het is 3-pyridyl and n is the integer 2.

4. The compound of claim 1 wherein $Ar_1$ is 2- or 4-chloro-, or 2- or 4-fluorophenyl; $Ar_2$ is 4-chloro- or 4-fluorophenyl; Het is 3-pyridyl; and n is the integer 2.

5. A fungicidal composition comprising a fungicidally effective amount of the compound of claim 1 and an agronomically acceptable inert carrier.

6. A fungicidal composition comprising a fungicidally effective amount of the compound of claim 2 and an agronomically acceptable inert carrier.

7. A fungicidal composition comprising a fungicidally effective amount of the compound of claim 3 and an agronomically acceptable inert carrier.

8. A fungicidal composition comprising a fungicidally effective amount of the compound of claim 4 and an agronomically acceptable inert carrier.

9. A method of controlling fungi comprising contacting said fungi or the locus of said fungi with a fungicidally effective amount of a compound of the formula:

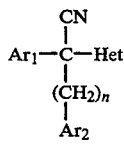

wherein $Ar_1$ is selected from an optionally substituted $C_6$ to $C_{10}$ aryl group with up to three substituents independently selected from the group consisting of halogen, nitro, cyano, $(C_1-C_{12})$ alkyl, $(C_1-C_{12})$ haloalkyl, $(C_3-C_8)$ cycloalkyl, $(C_5-C_8)$ cycloakkenyl, $(C_2-C_{12})$ alkenyl, $(C_2-C_{12})$ alkynyl, $(C_1-C_{12})$ alkoxy, $(C_1-C_{12})$ haloalkoxy, $(C_1-C_{12})$ alkylthio, $(C_1C_{12})$ alkylsulfinyl, $(C_1-C_{12})$ alkylsulfonyl, phenoxy, phenyl, phen$(C_1-C_{12})$alkyl, phen$(C_2-C_{12})$ alkenyl, phen$(C_2-C_{12})$alkynyl and $(C_5-C_6)$cycloalkyl $(C_1-C_6$alkyl; $Ar_2$ is an optionally substituted $(C_6-C_{10})$ aryl group wherein the substituents are independently selected from the substituents enumerated above for $Ar_1$; or $Ar_2$ may be thiopheneyl or furanyl; Het is a pyridyl ring; n is the integer 2 or 3; and the agronomically acceptable enantiomorphs, acid addition salts and metal complexes thereof.

10. The method of claim 9 wherein $Ar_1$ and $Ar_2$ are independently selected from phenyl or .phenyl substituted with up to two substituents selected from the group consisting of methyl, halomethyl, halogen, and alkoxy; and Het is a pyridyl ring; n is the integer 2 or 3; and agronomically acceptable enantiomorphs and acid salts thereof.

11. The method of claim 9 wherein $Ar_1$ is phenyl or 2- or 4-halosubstituted phenyl; $Ar_2$ is phenyl or 3- or 4-halosubstituted phenyl; Het is 3-pyridyl and n is the integer 2.

12. The methyl of claim 9 wherein $Ar_1$ is 2- or 4-chloro-, or 2- or 4-fluorophenyl; $Ar_2$ is 4-chloro- or 4-fluorophenyl; Het is 3-pyridyl; and n is the integer 2.

* * * * *